US009433389B2

(12) United States Patent
D'Souza et al.

(10) Patent No.: US 9,433,389 B2
(45) Date of Patent: Sep. 6, 2016

(54) METHOD FOR MONITORING THE ACCURACY OF TISSUE MOTION PREDICTION FROM SURROGATES

(75) Inventors: Warren D'Souza, Timonium, MD (US); Kathleen Malinowski, Seattle, WA (US); Thomas McAvoy, Ellicott City, MD (US)

(73) Assignees: UNIVERSITY OF MARYLAND, BALTIMORE, Baltimore, MD (US); UNIVERSITY OF MARYLAND, COLLEGE PARK, College Park, MD (US)

( * ) Notice: Subject to any disclaimer, the term of this patent is extended or adjusted under 35 U.S.C. 154(b) by 1027 days.

(21) Appl. No.: 13/531,044

(22) Filed: Jun. 22, 2012

(65) Prior Publication Data

US 2013/0018232 A1 Jan. 17, 2013

Related U.S. Application Data

(60) Provisional application No. 61/506,667, filed on Jul. 12, 2011.

(51) Int. Cl.
```
A61B 6/03     (2006.01)
A61B 6/12     (2006.01)
G06F 19/00    (2011.01)
A61B 6/00     (2006.01)
```
(Continued)

(52) U.S. Cl.
CPC .............. *A61B 6/12* (2013.01); *A61B 6/5217* (2013.01); *A61N 5/1049* (2013.01); *G06F 19/3437* (2013.01); *A61B 5/113* (2013.01); *A61N 5/1037* (2013.01); *A61N 5/1067* (2013.01)

(58) Field of Classification Search
CPC A61B 1/00186; A61B 5/0035; A61B 5/004; A61B 2576/00; A61B 6/12; A61B 6/5217; G06F 19/3437; A61N 5/1049
USPC .................................................. 600/300, 310
See application file for complete search history.

(56) References Cited

U.S. PATENT DOCUMENTS

| 8,042,209 B2 | 10/2011 | D'Souza et al. | |
| 2004/0092815 A1* | 5/2004 | Schweikard | A61B 6/12 600/425 |
| 2005/0054916 A1* | 3/2005 | Mostafavi | A61B 6/504 600/427 |

(Continued)

OTHER PUBLICATIONS

Hoogeman, M. et al., Clinical accuracy of the respiratory tumor tracking system of the cyberknife: assessment by analysis of log files, Int. J. Radiat. Oncol. Biol. Phys., 74(1), 297-303 (2009).

(Continued)

*Primary Examiner* — Christopher D Koharski
*Assistant Examiner* — Michael Carey
(74) *Attorney, Agent, or Firm* — Wenderoth, Lind & Ponack, L.L.P.

(57) ABSTRACT

A system and method for indirectly monitoring the position of a target inside a body is disclosed. The method includes generating position data associated with one or more surrogate devices and predicting a location of the target from the position data based on a target position model that establishes a relationship between an actual location of the target and the position data of the one or more surrogate devices. The method also includes determining that the predicted location of the target deviates from the actual location of the target when an analysis of an error prediction model results in a confidence threshold being exceeded.

20 Claims, 9 Drawing Sheets

(51) Int. Cl.
*A61N 5/10* (2006.01)
*A61B 5/113* (2006.01)

(56) References Cited

U.S. PATENT DOCUMENTS

2010/0198101 A1* 8/2010 Song .................. A61B 5/0536
600/547
2012/0004518 A1 1/2012 D'Souza et al.

OTHER PUBLICATIONS

Berbeco, R. et al., Residual motion of lung tumours in gated radiotherapy with external respiratory surrogates, Phys. Med. Biol., 50, 3655-3667 (2005).
Vedam, S. et al., Quantifying the predictability of diaphragm motion during respiration with a noninvasive external marker, Med. Phys. 30(4), 505-513 (2003).
Qiu, P. et al., Inferential modeling and predictive feedback control in real-time motion compensation using the treatment couch during radiotherapy, Phys. Med. Biol., 52, 5831-5854 (2007).
Kupelian. P. et al., Multi-institutional clinical experience with the Calypso system in localization and continuous, real-time monitoring of the prostate gland during external radiotherapy, Int. J. Radiat. Oncol. Biol. Phys., 67(4), 1088-1098 (2007).
Shirato, H. et al., Four-dimensional treatment planning and fluoroscopic real-time tumor tracking radiotherapy for moving tumor, Int. J. Radiat. Oncol. Biol. Phys., 48(2), 435-442 (2000).
Ozhasoglu, C. et al., Issues in respiratory motion compensation during external-beam radiotherapy, Int. J. Radiat. Oncol. Biol. Phys., 52(5), 1389-1399 (2002).
Ionascu, D. et al., Internal-external correlation investigations of respiratory induced motion of lung tumors, Med. Phys., 34(10), 3893-3903 (2007).
Hugo, G. et al., Changes in the respiratory pattern during radiotherapy for cancer in the lung, Radiother. Oncol., 78, 326-331 (2006).
Hoisak, J. et al., Correlation of lung tumor motion with external surrogate indicators of respiration, Int. J. Radiat. Oncol. Biol. Phys., 60(4), 1298-1306 (2004).
Malinowski, K. et al., Mitigating errors in external respiratory surrogate-based models of tumor position, Int. J. Radiation Oncol. Biol. Phys., 82(5), e709-e716, (2012).
Ergon, R., Informative PLS score-loading plots for process understanding and monitoring, Journal of Process Control, 14, 889-897 (2004).
Seppenwoolde, Y. et al., Precise and real-time measurement of 3D tumor motion in lung due to breathing and heartbeat, measured during radiotherapy, Int. J. Radiat. Oncol. Biol. Phys., 53(4), 822-834 (2002).
Jackson, J.E. et al., Control procedures for residuals associated with principal components analysis, Technometrics, 21(3), 341-349 (1979).
Lee, J.M. et al., Statistical monitoring of dynamic processes based on dynamic independent component analysis, Chem. Eng. Sci., 59, 2995-3006 (2004).
Seppenwoolde, Y. et al., Accuracy of tumor motion compensation algorithm from a robotic respiratory tracking system: a simulation study, Med. Phys., 34(7), 2774-2784 (2007).

* cited by examiner (a)

(b)

(a)

(b)

(c)

METHOD FOR MONITORING THE ACCURACY OF TISSUE MOTION PREDICTION FROM SURROGATES

CROSS-REFERENCE TO RELATED APPLICATIONS

The present application claims priority to U.S. Provisional Application Ser. No. 61/506,667, filed Jul. 12, 2011, which is fully incorporated herein by reference.

STATEMENT OF FEDERALLY SPONSORED RESEARCH

This invention was made with government support under grant No. CA124766 awarded by the National Institutes of Health. The government has certain rights in the invention.

FIELD OF THE INVENTION

The present invention relates generally to methods and devices for monitoring internal targets in a body. More specifically, the present invention relates to methods of indirectly monitoring the position of internal anatomical targets or implanted objects in a body in real time.

BACKGROUND OF THE INVENTION

Radiation beam gating and tumor tracking technologies are designed to manage tumor motion in real time during radiotherapy. The performance of these devices depends on the ability to rapidly and accurately localize the tumor. Direct tumor tracking systems are limited to electromagnetic tracking for use in the prostate exclusively because continuous x-ray imaging systems impart ionization radiation over the duration of the treatment. Thus, many systems, rather than correct due to the respiration-induced tumor motion, determine the position of the tumor from surrogates of respiration. See Hoogeman M, Prévost J B, Nuyttens J, Pöll J, Levendag P, Heijmen B. Clinical accuracy of the respiratory tumor tracking system of the Cyberknife: assessment by analysis of log files. Int. J. Radiat. Oncol. Biol. Phys. 74, 297-303 (2009); Berbeco R I, Nishioka S, Shirato H, Chen G T, Jiang S B. Residual motion of lung tumours in gated radiotherapy with external respiratory surrogates. Phys. Med. Biol. 50, 3655-3667 (2005); Vedam S S, Kini V R, Keall P J, Ramakrishnan V, Mostafavi H, Mohan R. Quantifying the predictability of diaphragm motion during respiration with a noninvasive external marker. Med. Phys. 30, 505-513 (2003); Qiu P, D'Souza W D, McAvoy T J, Ray Liu K J. Inferential modeling and predictive feedback control in real-time motion compensation using the treatment couch during radiotherapy. Phys. Med. Biol. 52, 5831-5854 (2007); Kupelian P, Willoughb T, Mahadevan A, Djemil T, Weinstein G, Jani S, Enke C, Slberg T, Flores N, Liu D, Beyer D, Levine L. Multi-institutional clinical experience with the Calypso system in localization and continuous, real-time monitoring of the prostate gland during external radiotherapy. Int. J. Radiat. Oncol. Biol. Phys. 67, 1088-1098 (2007); and Shirato H, Shimizu S, Kitamura K, Nishioka T, Kagei K, Hashimoto S, Aoyama H, Kunieda T, Shinohara N, Dosaka-Akita H, Miyasaka K. Four-dimensional treatment planning and fluoroscopic real-time tumor tracking radiotherapy for moving tumor. Int. J. Radiat. Oncol. Biol. Phys. 48, 435-442 (2000).

Methods for estimating tumor position from respiratory surrogates range from simple respiratory surrogate signal scaling to mathematically complex multi-input surrogate-based models used to determine tumor position. Regardless of its form, the surrogate-based model only remains valid while there is a constant relationship between the tumor position and the respiratory surrogate signals. However, the tumor-surrogate relationship can change during the treatment fraction, thereby causing the surrogate-based model to degrade over time. See Ozhasoglu C, Murphy M. Issues in respiratory motion compensation during external-beam radiotherapy. Int. J. Radiat. Oncol. Biol. Phys. 52, 1389-99 (2002); Ionascu D, Jiang S B, Nishioka S, et al. Internal-external correlation investigations of respiratory induced motion of lung tumors. Med. Phys. 34, 3893-3903 (2007); Hugo G, Vargas C, Liang J, Kestin L, Wong J W, Yan D. Changes in the respiratory pattern during radiotherapy for cancer in the lung. Radiother. Oncol. 78, 326-331 (2006); Hoisak J D P, Sixel K E, Tirona R, et al. Correlation of lung tumor motion with external surrogate indicators of respiration. Int. J. Radiat. Oncol. Biol. Phys. 60, 1298-1306 (2004); and Malinowski K, McAvoy T J, George R, et al. Mitigating errors in external respiratory surrogate-based models of tumor position. [In press]; and Seppenwoolde Y, Berbeco R I, Nishioka S, Shirato H, Heijmen B. Accuracy of tumor motion compensation algorithm from a robotic respiratory tracking system: a simulation study. Med. Phys. 34, 2774-2784 (2007).

Currently available systems must frequently interrupt treatment to validate the surrogate-based model through additional ground-truth measurements of tumor position. The Cyberknife Synchrony™ system, for instance, validates its model at a user-selected rate of about once per minute by localizing tumor-implanted fiducials with stereoscopic radiographs. This technique of pre-scheduled intermittent data collection for model validation has at least three shortcomings: (1) if changes to the tumor-surrogate relationship occur shortly after one tumor localization, then the model can have large localization errors until the changes are detected at the next tumor localization; (2) added and unnecessary tumor localizations not leading to model updates result in unnecessary exposure to ionizing radiation; and (3) pausing for image-based tumor localization extends the duration of the treatment fraction.

SUMMARY OF THE INVENTION

An object of embodiments of the present invention is to substantially address the above and other concerns, and provide improved target prediction. A disclosed method of indirectly monitoring the position of a target inside a body comprises generating position data associated with one or more surrogate devices, predicting a location of the target from the position data based on a target position model that establishes a relationship between an actual location of the target and the position data of the one or more surrogate devices, and determining that the predicted location of the target deviates from the actual location of the target when an analysis of an error prediction model results in a confidence threshold being exceeded.

Also disclosed is a system for indirectly monitoring the position of a target inside a body. The system generally includes a sensor device configured to provide position data, and a processor for predicting a location of the target from the position data using a target position model that determines a relationship between the target and the one or more surrogate devices and further determines that the predicted location of the target has deviated from the actual location of the target if an analysis of an error prediction model results in a confidence threshold being exceeded.

Another disclosed method for indirectly monitoring the position of a target inside a body comprises generating a target position model that predicts a location of a target of a patient and generating an error prediction model that determines whether the predicted location of the target has deviated from the actual location of the target, generating position data based on the respective positions of one or more surrogate devices coupled to the patient, predicting a location of the target using the target position model and the position data, delivering a medical treatment to the patient based on the target position model during a treatment period, determining whether the predicted location of the target has deviated from the actual location of the target using only the position data and the error prediction model during the treatment period, and when the predicted location of the target has deviated from the actual location of the target, pausing delivering of the medical treatment, updating the target prediction model, and resuming the delivering of the medical treatment.

BRIEF DESCRIPTION OF THE DRAWINGS

The various objects, advantages and novel features of the exemplary embodiments of the present invention will be more readily appreciated from the following detailed description when read in conjunction with the appended drawings, in which.

DETAILED DESCRIPTION OF EXEMPLARY EMBODIMENTS

Figure 1:
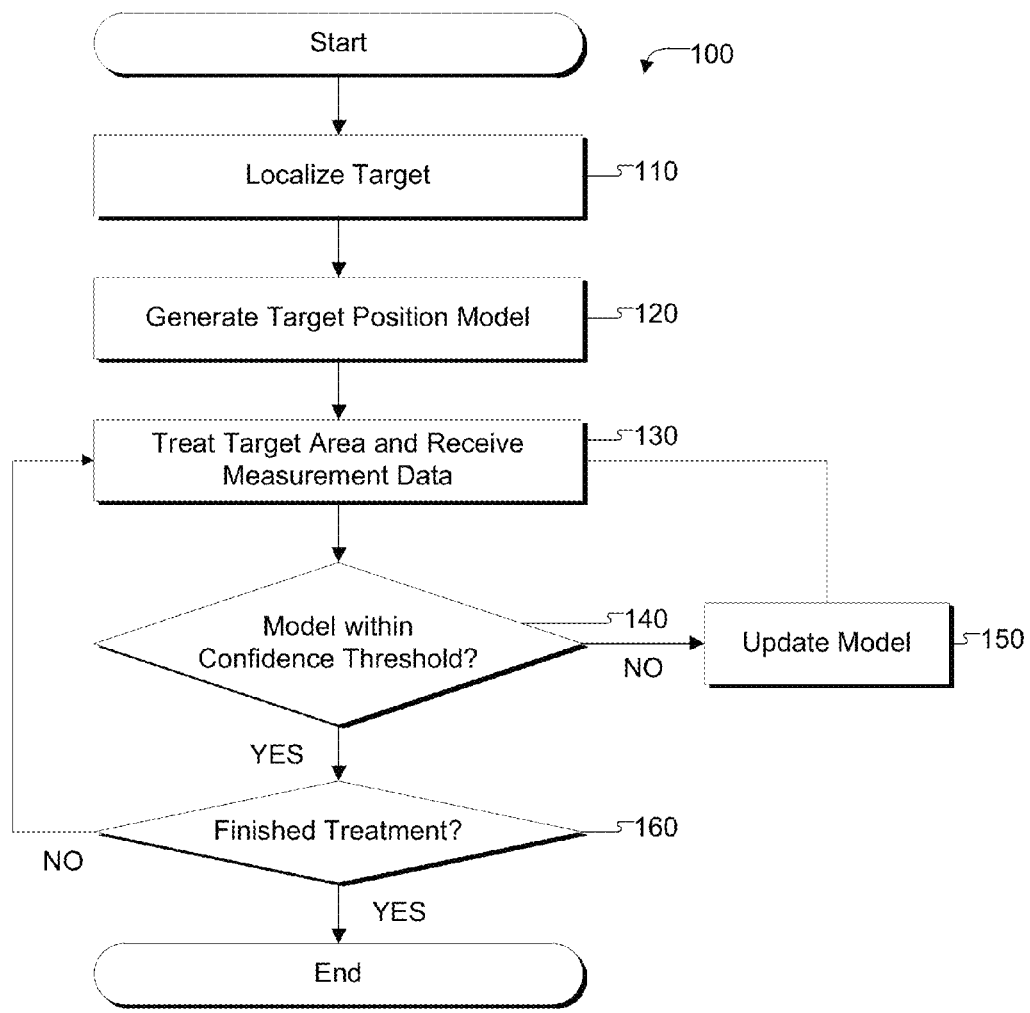
FIG. 1 is a flow diagram of an example process for indirectly monitoring the position of a target inside a patient.

Methods and apparatus for indirectly monitoring the position of a target inside of a patient are generally described herein. As will be appreciated by one skilled in the art, there are numerous ways of carrying out the examples, improvements and arrangements of the methods disclosed herein. Although reference is made to the exemplary embodiments depicted in the drawings and the following descriptions, the embodiments disclosed herein are not meant to be exhaustive of the various alternative designs and embodiments that are encompassed by the disclosed invention.

Reference is now made in detail to the example embodiments of the invention, which, together with the drawings and the following examples including prophetic examples, serve to explain the principles of the invention. These embodiments are described in detail to enable those skilled in the art to practice the invention, and it is to be understood that other embodiments may be utilized without departing from the spirit and scope of the present invention. Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, the example methods, devices and materials are now described.

In one example, a real time sensor system is used to determine the position of the surface of a patient during treatment. For instance, respiratory motion causes movement within the thoracic cavity, thereby causing the surfaces of the patient to move. One example real time sensor system can be implemented by optical sensors that receive position data provided by surrogate measurement devices disposed on the patient's body. For example, a DYNATRAC™ system consists of three wall-mounted infrared cameras that transmit received data to a processing device. In such a system, up to 20 optical reflectors are fixed to the patient to reflect infrared energy at discrete positions of the patient's surface, which are received by the infrared cameras and converted into position data in the system. However, any suitable real time sensor system may be used such as the Elektra Sentinel™, for example. In other examples, respiratory motion is measured via the surface of the body using light in the visible or invisible portion of the spectrum. In another example, the respiratory motion may be directly measured using at least one of an ultrasonic device, cameras, lasers, and a strain gauge wrapped around the body. The position of the patient may also be measured via any combination of suitable devices.

In other examples, the measured parameters include, but are not limited to, blood oxygen level measured using a pulse oxygen monitor, heart electrical activity measured using an electrocardiogram (EKG), brain electrical activity measured using an electroencephalogram (EEG), air flow measured using a spirometer, differential temperature of air flow measured using a thermocouple, and respiratory motion.

FIG. 1 is a flow diagram that illustrates an example process 100 for monitoring the position of a target inside of a patient. In the example of FIG. 1, one or more surrogate measurement devices are disposed on the body of the patient for providing position data of the measurement devices. As noted above, the surrogate measurement devices may be any suitable device to measure the position of a surface of the patient. At step 110, the target in the patient is localized by using imaging to create a relationship between the surrogates and the targets. For instance, radiograph images of the fiducial markers are captured and used to determine the position of the target. In other examples, non-invasive tomographic images are used to determine the position of the target. Using the localized position data and the position data from the surrogate measurement devices, a relationship between the surrogate measurement devices and the target can be determined. However, because the patient's body is not stagnant due to respiratory motion, the relationship between the surrogate measurement devices and the target changes during the treatment period.

The example process 100 at step 120 generates a surrogate-based model that generally predicts the position of the target and monitors the prediction of the target location.

Generally, the model is a relationship between variables in the form of mathematical equations and describes how one or more variables are related. In one example, the model comprises a target position model that may be generated via a partial least squares analysis using the localized position data of the target. The target position model predicts the position of the target based on the localization data and measurement data from the surrogate measurement devices. The target position model is described in more detail in U.S. Pat. No. 8,042,209 and U.S. patent application bearing Ser. No. 13/172,010, the disclosures of which are herein incorporated by reference.

One exemplary surrogate-based target position model is created by developing a model predictive control (MPC) system, such as an internal model controller (IMC) that accounts for the temporal response of a device being moved when subjected to a command to move a certain amount. A time-series of measurements of a patient state are received by a real-time state sensor system, such as a DYNA-TRACK™ system. Synchronized with the measurements of the patient state, a time-series of non-invasive tomographic images of the target site are also received. Using the tomographic images, a time-series of target site positions is derived based on the tumor position's center-of-mass or the centroid of the tumor volume. A partial least squares (PLS) calculation is then used to derive the patient specific correlation between the patient state and target site position from the derived time-series of target site positions and the time-series of the patient state.

According to a further embodiment, the surrogate-based model includes an error prediction model that monitors the target position models for prediction errors. In one example, the error prediction model comprises a measurement monitoring model that monitors the measurement data and determines if the relationship of the measurement data changes. The error prediction model may also include an input variance model that computes the amount of variance of the measurement data not captured by the target position model. The measurement monitoring model and the input variance model are generally used to determine the accuracy of the target position model.

At step 130, the target is treated according to the target position model while the example process 100 receives measurement data from the surrogate measurement devices. The error prediction model (e.g., the measurement monitoring model and/or the input variance model, etc.) is continuously analyzed at step 140 using the received measurement data to verify the accuracy of the target position model. Specifically, statistical analysis is used to verify the accuracy of the target position model using a confidence threshold for the input variance model and another confidence threshold for the measurement monitoring model.

In one example, the measurement monitoring model computes the Hotelling statistic, $T^2$, which characterizes the amount of variation in the inputs to the target position model. Aberrant $T^2$ values indicate that the relationship between measurement data from the surrogate measurement devices has changed and that the model must be updated to accommodate the new measurement data. In another example, the input variance model is an input variable squared prediction error model, $Q^{(x)}$, which computes the amount of variance that is not captured by the target position model. The measurement monitoring model and the input variance model are independent and may be used in conjunction to determine if there are potential errors in the model. One skilled in the art would recognize any suitable statistical analysis may be used to continually assess the reliability of the model.

The confidence threshold for each statistical analysis is either fixed or may be set by a practitioner prior to treatment. Adjustments to the confidence thresholds will impact the degree of sensitivity and specificity of any statistical measures.

Sensitivity measures the proportion of errors greater than a target localization error limit that are detected by the one or more statistical measures. The target localization error limit is the distance that the one or more statistical analysis may predict the model may be deviating from the actual target location. This limit may be fixed or may be set by the practitioner prior to treatment. It may be between about 0.5 mm and about 10 mm. In some examples the tumor localization error limit is between about 2 mm and about 5 mm. In yet other examples the tumor localization error limit is about 3 mm.

Specificity is the proportion of errors less than the target localization error limit that are identified by the statistical analysis as likely to be less than the target localization error limit. Sensitivity and specificity have an inverse relationship to each other. Generally, the confidence thresholds may be between about 50% and 99%. In some examples the confidence threshold is between about 60% and 90%. In yet other examples the confidence level threshold is set to about 70%.

If the input variance model and/or measurement monitoring model described above are not within the confidence threshold at step 140, then the target position model may not be accurate and, as such, the treatment of the patient is paused so that the target position model can be updated at step 150. In one example, after pausing treatment, the target in the patient is localized again and updated localized position data of the target is generated. The target position model is updated by incorporating the new localized position data with previous localization position data. The input variance model and measurement monitoring model may also be updated based on the new localized position data and the updated target position model at step 150. After updating any of the models at step 150, the treatment of the patient is resumed at the step 130.

Referring back to step 140, if the input variance model and/or measurement monitoring model are within the confidence threshold, then the example process 100 determines that the target position model is accurate and treatment continues by proceeding to step 160 where the example process 100 determines if the treatment is finished. If treatment is not finished at step 160, the example process 100 returns to step 130 to continue treatment of the patient by monitoring the models as described above. If the treatment is finished at step 160, the treatment of the patient is stopped and the example process 100 ends.

The examples described herein may be implemented to increase the targeting accuracy of any real-time motion compensation device, including radiation gating systems. The methods may be integrated with the selected real-time motion compensation device in a variety of ways. For instance, the examples may be implemented in a Cyberknife Synchrony™ system or may be implemented in a computer readable medium on a separate device. Various forms of computer readable media may be involved in carrying one or more sequence of instructions or data or both to the real-time motion compensation device.

Additional details of exemplary processes that may be used to perform all or part of the example process 100 are described below in relation to two studies performed using databases from prior treatments. The first study describes the model in further detail.

Data

A database of Cyberknife Synchrony™ system log files consisting of 130 fractions from 63 lung cancer patients, 10 fractions from 5 liver cancer patients, and 48 fractions from 23 pancreas cancer patients was analyzed. The Cyberknife Synchrony™ log files included independently measured but concurrent 3D tumor and external marker localizations captured once every 3 beams (or an average of 63 sec apart). Tumors were localized as the centroid of a set of implanted fiducial markers measured in stereoscopic radiographs. Three LED surrogate markers affixed to the torso were localized optically by a camera system to generate position data of the surface of the patient. The position of the tumor was aligned in time with the LED surrogate markers according to the timestamps in the system log files. Each treatment fraction dataset consisted of at least 40 (ranging from 40 to 112, median of 61) concurrent tumor and external sensor localizations. The data was truncated to include only the longest period of uninterrupted treatment in each fraction and to exclude both pre-treatment image acquisitions and unplanned radiographs acquired during treatment for the purpose of repositioning the patient.

Partial Least Squares (PLS) Regression for Predicting Tumor Positions

In this example, a Partial Least Squares (PLS) target position model for determining tumor position from the surrogate marker displacements was developed for each treatment fraction. Generally, PLS is a method for modeling relationships between an input matrix, X, and an output matrix, Y, by means of scores, which may also be called latent variables. The input matrix is composed of m respiratory surrogate signals, $x_i$ for $i=1$ to m, such that $X=[x_1\ x_2\ \ldots\ x_m]$. The input matrix can also be represented as n rows, each consisting of a set of respiratory surrogate measurements, $z_i$ for $i=1$ to n, captured at one point in time such that $X=[z_1\ z_2\ \ldots\ z_n]^T$. The n×3 output, Y, consists of 3 tumor displacement dimensions and n samples. Each column of the input and output matrices was mean-centered and scaled to unit-variance.

In this example, the iterative SIMPLS algorithm was used to decompose X and Y into $X=T \cdot W^T$ and $Y=U \cdot Q^T$, for n×m matrix T of input scores, n×m matrix U of output scores, m×m matrix W of input weights, and p×m matrix Q of output weights. See du Jong S. SIMPLS: an alternative approach to partial least squares regression. Chemometrics and intelligent laboratory systems. 18, 251-263 (1993). The first column of T, $t_1$, was given by $t_1 = X \cdot X^T \cdot Y / \text{norm}(X \cdot X^T \cdot Y)$. The first column of W, $w_1$, and the first X basis, $v_1$, were each equal to one. The following iterative regression process was then repeated for $i=1$ to m. First, the Y loadings and scores were calculated as $q_i = Y^T \cdot t_i$ and $u_i = Y^T \cdot q_i$, respectively. Next, the X basis was updated with each iteration as $v_i = v_{i-1} - V_{i-1} \cdot (V_{i-1}^T \cdot (t_i^T \cdot X)^T)$, where $V_{i-1} = [v_1, v_2, \ldots, v_{i-1}]$. Finally, subsequent X weights and scores were calculated as $w_i = (S_{i-1} - v_i \cdot (v_i^T \cdot S_{i-1})) \cdot q_i$ and $t_i = X \cdot w_i$.

Because the PLS algorithm determines scores in order of decreasing contribution to the PLS model, utilizing only the first A of m factors serves to select the input information most relevant to the outputs. Thus the score and loading matrices were compressed as $X = \hat{T} \cdot \hat{W} + E$ and $Y = \hat{U} \cdot \hat{Q} + F$, where $\hat{T}$ was the n×A matrix $\hat{T} = [t_1, t_2, \ldots, t_A]$, $\hat{W}$ was the m×A matrix $\hat{W} = [w_1, w_2, \ldots, w_A]$, $\hat{U}$ was the n×A matrix $\hat{U} = [u_1, u_2, \ldots, u_A]$, and $\hat{Q}$ was the p×A matrix $\hat{Q} = [q_1, q_2, \ldots, q_A]$. The residual matrices were E and F. Cross-validation was used to select the appropriate number of factors, A, for each training dataset. The regression coefficient matrix, B, was given by $\hat{B} = \hat{R} \cdot \hat{Q}^T$, where $\hat{R} = [r_1, r_2, \ldots, r_A]$ and $\hat{Q} = [q_1, q_2, \ldots, q_A]$.

Tumor position using the target position model was determined as $\hat{Y} = X \cdot \hat{B}$ or, from a single new set of measurements, $z_{new}$, as $\hat{y}_{new} = z_{new} \cdot \hat{B}$. The inferential model error, e, was calculated as $e = \sqrt{\Sigma(\hat{y}_{new} - y_{new})^2}$, the Euclidean distance between PLS-predicted tumor positions ($\hat{y}_{new}$) and radiographically measured tumor predictions ($y_{new}$).

Tumor Motion Models and Model Monitoring

Two PLS models were created for each training dataset: one for prediction of the target position and a second for monitoring the target position model for prediction errors. The input projection process leads to models that can more accurately predict tumor displacement from surrogate marker motion. See Malinowski K, McAvoy T J, George R, et al. Mitigating errors in external respiratory surrogate-based models of tumor position. However, projecting the inputs degrades the ability to monitor the target-position model for changes. The PLS models differed in their input matrix, X.

The first 10 samples (n=10) of concurrent surrogate marker and tumor localizations in the treatment fraction dataset were used as training data for the models. For the monitoring model, X was a 10×9 matrix describing the 3D positions of three surrogate markers at 10 samples. For the target prediction model, X was a 10×3 matrix in which each column was a one-dimensional (1D) representation of the three-dimensional (3D) motion of one of the surrogate markers. These 1D surrogate signals were created by orthogonally projecting the surrogate marker measurements captured during the training data acquisition period onto a line. This line was defined by the displacements' 3D mean, M, and first principal component vector. The 1D representation for each sample was defined as the distance between the projected point and M.

Figure 2:
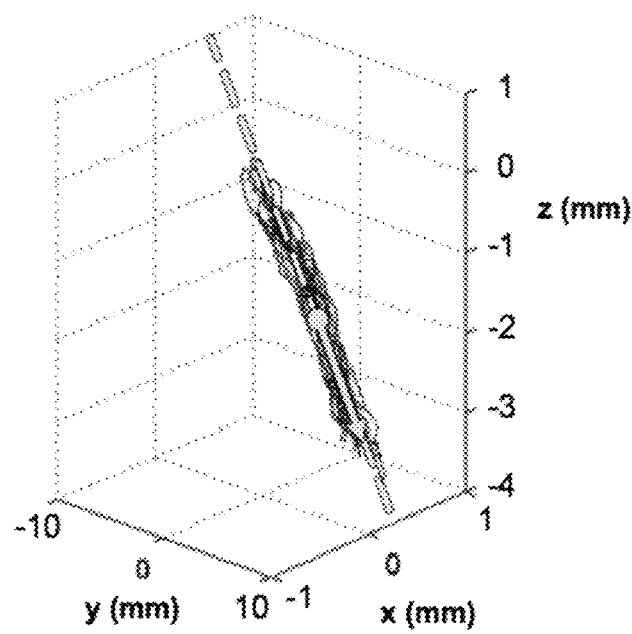
FIG. 2 is an example of the surrogate marker projection process.
Figure 2:
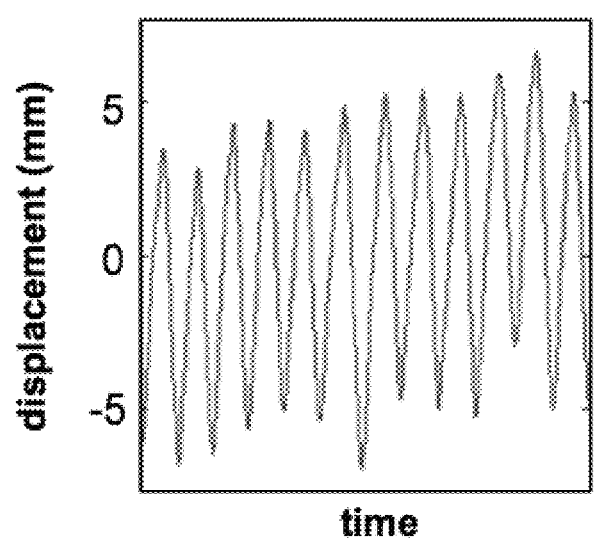

FIG. 2 depicts the surrogate marker projection process. FIG. 2(a) is an example of 3D surrogate marker motion data, depicted as a blue dot, including its mean and first principal component vector, depicted by a blue arrow, and its projection line, depicted by a dashed line. FIG. 2(b) is a 1D representation of the 3D data of FIG. 2(a).

Respiratory Surrogate-Based Monitoring Metrics

The surrogate measurement data captured during the initial model development period was compared to surrogate measurement data captured during the treatment fraction. Using this technique, it can be determined if the real time target prediction is accurate based on the target-position model using the measurement data. Thus, the quality of the target-position model can be monitored without stopping treatment to explicitly measure the target and determine the actual tumor position.

For each 1×3 vector of inputs, $z_i$, an associated score vector, $\hat{t}_i$, was calculated as $\hat{t}_i^T = z_i \cdot \hat{W}$, where $\hat{W}$ was the compressed weight vector calculated as part of the PLS regression process. The scores were then used to calculate the associated Hotelling statistic, $T^2$, and input variable squared prediction error, $Q^{(X)}$, for the measurement data. The $T^2$ and $Q^{(X)}$ statistics rely on measurement data from the surrogate markers exclusively and do not utilize target position measurements from radiographic images.

Hotelling's $T^2$ statistic characterizes the amount of variation in the measurement data input into the target position model. Aberrant $T^2$ values indicate that the relationship between measurement data has changed and that the target position model must be extrapolated to fit the new measurement data. $T^2$ was calculated as $T^2 = t_{new}^T \cdot S^{-1} \cdot t_{new}$ from the estimated training data score covariance matrix, $$S = \frac{\hat{T}^T \cdot \hat{T}}{n-1}.^{16}$$

The input variable squared-prediction-error, $Q^{(X)}$, measures the data in a row of the residual matrix, E, in the compression step $X = \hat{T} \cdot \hat{W} + E$ described above. This metric determines the amount of variance not captured by the scores, $\hat{T}$, which is used to in the target position model as described above. An increase in $Q^{(X)}$ over time indicates that less of the information in the measurement data is being used by the target position model, thereby decreasing the accuracy of the target position model. $Q^{(X)}$ was given by $$Q^{(X)} = \sum_{i=A+1}^{m} (\hat{z}_i - z_i)^2$$

for sample i, where $\hat{z}_i = t_i \cdot \hat{W}$ and represents the surrogate marker measurement vector, $z_i$, compressed to 1 score (A=1). See MacGregor J F and Kourti T. Statistical process control of multivariate processes. Control Eng. Practice. 3, 403-414 (1995).

Performance of Respiratory Surrogate-Based Monitoring

Large Error Detection

Treatment fraction-specific limits on $T^2$ and $Q^{(X)}$ were calculated and tested for $(1-\alpha)$ percentile confidence limits for $0<\alpha<1$. The confidence limits were used as control limits for $T^2$ and $Q^{(X)}$. For $T^2$, confidence limits were determined from $$T_\alpha^2 = \frac{(n^2-1)A}{n(n-A)} F_\alpha(A, n-A),$$

where n=10 was the quantity of training samples used to generate the model, one score was used in the PLS model created to monitor the tumor localization model (A=1), and $F_\alpha(A, n-A)$ was the upper (100%). ($\alpha$) critical point of the F distribution with (A, n-A) degrees of freedom. Confidence limits on $Q^{(X)}$ were calculated through the Jackson-Mudholkar[18] formula, $$Q_\alpha = \theta_1 \left[ 1 - \frac{\theta_2 h_0(1-h_0)}{\theta_1^2} + \frac{z_\alpha \sqrt{2\theta_2 h_0^2}}{\theta_1} \right]^{1/h_0},$$

in which $z_\alpha$ is the upper (100%). ($\alpha$) critical point of the normal distribution, $$\theta_j = \sum_{i=A+1}^{m} \lambda_i^j,$$

n=10, $$h_0 = 1 - \frac{2\theta_1 \theta_3}{3\theta_2^2},$$

and $\lambda_i$ is the ith eigenvalue of $(\hat{z}_{new,i} - z_{new,i})^T (\hat{z}_{new,i} - z_{new,i})$.

The ability of $T^2$ and $Q^{(X)}$ to predict whether the target position model is accurate to within 3 mm was evaluated for each $\alpha$. Prediction of large (>3 mm) errors was based on whether $T^2$ or $Q^{(X)}$ exceeded the treatment fraction-specific confidence limits and was validated against radiographic measurements. To evaluate the performance of this method, sensitivity and specificity were explored under various conditions. Sensitivity and specificity were determined for: (1) $T^2$ confidence limit; (2) $Q^{(X)}$ confidence limit; and (3) the union of results from $T^2$ confidence limit and $Q^{(X)}$ confidence limit, in which the method predicts large error if either $T^2$ or $Q^{(X)}$ exceeds its respective confidence limit threshold. Receiver operating characteristic (ROC) analysis was performed to evaluate sensitivity versus specificity at any confidence limit between 0% and 100%.

In addition to the surrogate measurement data concurrent with the tumor displacement, the utility of past surrogate measurement data was evaluated for data up to 10 sec prior to the surrogate marker-based target localization. For this multiple measurement method, the proportion of $T^2$, $Q^{(X)}$, or $T^2 \cup Q^{(X)}$ values in the testing period that exceeded the confidence limit(s) was calculated. A threshold value for predicting large inferential model errors (for example, at least 10% of the measurements during the 5 sec prior to the tumor localization) was selected to maximize specificity at the target sensitivity.

Time to Error and Time to Alarm

For each treatment fraction and monitoring method, the times from the end of the training dataset to the first large error (time to error) and to the first Statistic Process Control (SPC)_based indication of large error (time to alarm) were determined. Results were compared to the timing of images captured by the Cyberknife Synchrony™ system that were taken to validate its own model during the treatment.

Effect of Tumor Site

Results were stratified by tumor site for lung (130 fractions) and pancreas (48 fractions) cases, using 2 sec of surrogate marker data preceding the tumor localization.

Results

Large Error Detection

Figure 3:
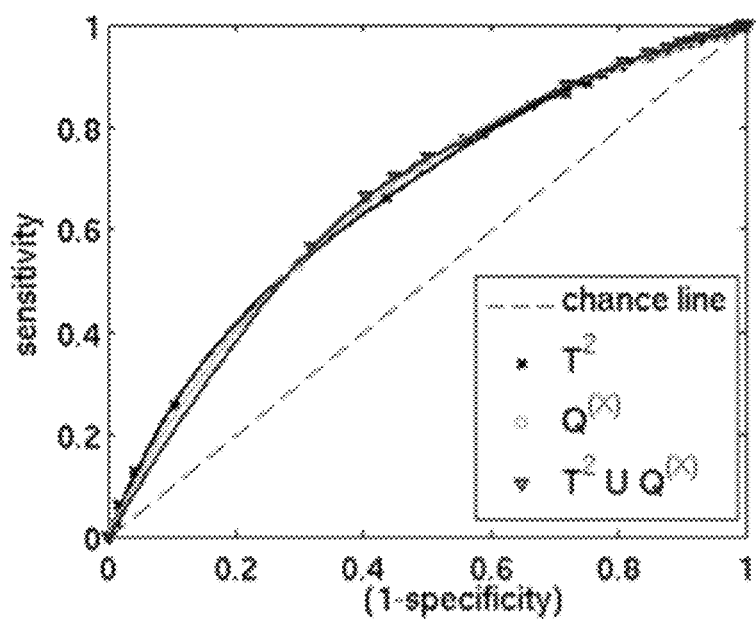
FIG. 3 depicts receiver operator characteristic (ROC) curves showing ability to predict localization errors exceeding 3 mm for various confidence levels.

The $T^2$ and $Q^{(X)}$ statistics were able to indicate such phenomena as large errors associated with gradual decreases in the target position model accuracy and transient surrogate marker tracking errors. All three SPC tests, $T^2$, $Q^{(X)}$, and $T^2 \cup Q^{(X)}$, were predictive of large errors. FIG. 3 depicts receiver operator characteristic (ROC) curves showing ability to predict localization errors exceeding 3 mm for various confidence levels. Sensitivity and specificity varied with confidence limit selection, with increasing sensitivity associated with decreased specificity. $T^2 \cup Q^{(X)}$ was associated with specificity 1-2% higher than either $T^2$ or $Q^{(X)}$ alone at 90-95% sensitivity (Table I).

TABLE I

Summary of monitoring performance for all tumor sites at 90% and 95% sensitivity.

| Method | Sensitivity | Specificity | Time to alarm mean | Time to alarm st. dev. |
|---|---|---|---|---|
| $T^2$ | 90% | 23% | 6.0 min | 8.8 min |
| $Q^{(X)}$ | 90% | 24% | 7.6 min | 9.9 min |
| $T^2 \cup Q^{(X)}$ | 90% | 24% | 7.2 min | 9.8 min |
| $T^2$ | 95% | 13% | 4.0 min | 8.1 min |
| $Q^{(X)}$ | 95% | 14% | 4.6 min | 8.1 min |
| $T^2 \cup Q^{(X)}$ | 95% | 15% | 5.3 min | 8.2 min |

$T^2$ and $Q^{(X)}$ did not increase monotonically, and $T^2$ in particular varied cyclically with the phase of respiration. Incorporating past measurements of surrogate measurement data improved the monitoring performance for $Q^{(X)}$ and $T^2 \cup Q^{(X)}$. For 95% sensitivity, the best specificity for $T^2 \cup Q^{(X)}$ was achieved by requiring that 5% of SPC measurements acquired over the past 3 sec exceed the confidence limit threshold.

An example of (a) $T^2$, (b) $Q^{(X)}$, and (c) tumor localization error versus time elapsed since the training data is disclosed. In (a) and (b), the localization errors occurred. The horizontal dashed lines represent control limits, and times in which the control limit is exceeded are shaded. In (c), the horizontal dashed line represents a 3 mm error limit, and radiographic tumor localizations errors are indicated at t=0.8 min and t=1.8 min by circled x's (⊗). It is likely that localization errors exceed 3 mm from 0.3 to 0.5 min and after 0.9 min, but radiographic validation is only possible at two moments over this 2 min period.

Time to Error and Time to Alarm

For the target position model used in this example, the mean (±standard deviation) time from the last tumor localization to an error >3 mm was 12±12 min for those fractions in which errors >3 mm. This mean time excludes the 6% of fractions in which no tumor position prediction error was >3 mm.

For the dataset, the mean time to alarm for the Cyberknife Synchrony™ system was 1.1 min. For SPC parameters giving the highest specificity at 90% sensitivity (Table I) using the target position model described above, the mean times from training data to indication of large errors (mean time to alarm) for $T^2$, $Q^{(X)}$, and $T^2 \cup Q^{(X)}$ were 6.0 min, 7.6 min, and 7.2 min, respectively. In 5% of the measured fractions, the error never exceeded 3 mm. However, there were no fractions for which neither $T^2$ nor $Q^{(X)}$ did not exceed the confidence limit threshold for at least one set of surrogate marker measurements.

Effect of Tumor Site

Figure 5:
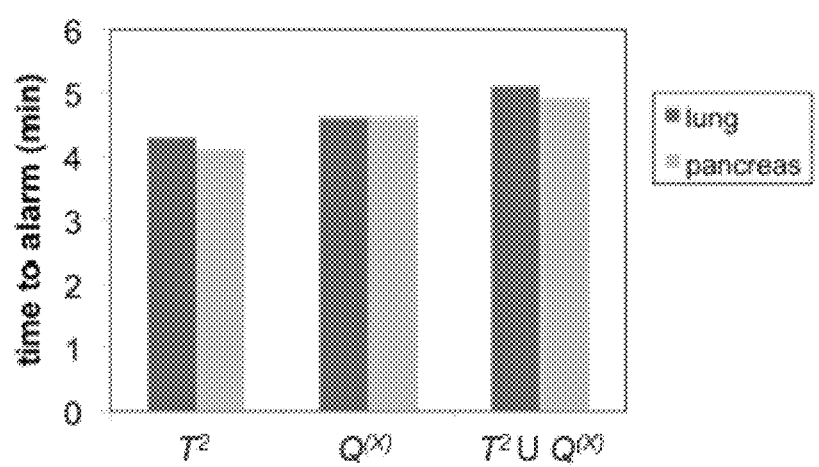
FIG. 5 is a representative comparison of mean time to alarm for lung and pancreas results using 2 seconds of data.

As depicted in FIG. 5, there was no significant difference between lung and pancreas cases in time to alarm. The specificities for each site were equal to the specificities for the pooled lung, liver, and pancreas results at 90-95% sensitivity given in Table I.

Discussion

The results of this example establish the feasibility of using SPC in online monitoring of the accuracy of real-time respiration-induced tumor motion models similar to the target position model described above. The error prediction models provided via the $T^2$ and $Q^{(X)}$ statistics, respectively, were able to indicate when the target position model errors exceeded 3 mm with high sensitivity. For 95% error prediction sensitivity, specificity was 15%, and the mean time to alarm was 5.3 minutes. Modest improvements in specificity were achieved by combining $T^2$ and $Q^{(X)}$ results and by expanding the input to include the previous 3 seconds of respiratory surrogate measurement data.

Real-time motion management systems rely on rapid, accurate tumor localization. For respiratory surrogate-based systems, current clinical practice is to establish a surrogate-based model before beginning treatment and then either to assume that the surrogate-based model will remain valid or to periodically validate the model according to a predetermined schedule. If the standard radiographic tumor localizations are too sparse, large targeting errors may occur during the treatment. Conversely, radiographic images captured while the surrogate model remains accurate causes unnecessary exposure to ionizing radiation and extending the duration of the treatment. Generally, timing of radiographic tumor localizations determines the accuracy of the model, but the patient-specific benefit of increasing the imaging frequency varies widely. As described above, a method for timing radiographic image acquisitions is implemented to update respiratory surrogate tumor motion models by relying exclusively on surrogate measurements to increase the time between radiographic tumor localizations.

Figure 4:
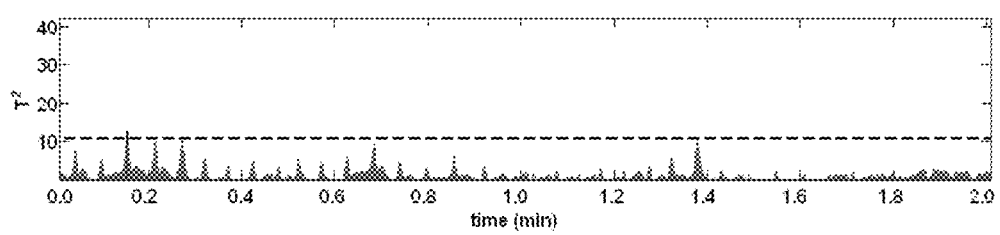
FIG. 4 is an example of (a) $T^2$, (b) $Q^{(X)}$, and (c) tumor localization error versus time elapsed since the training data.
Figure 4:
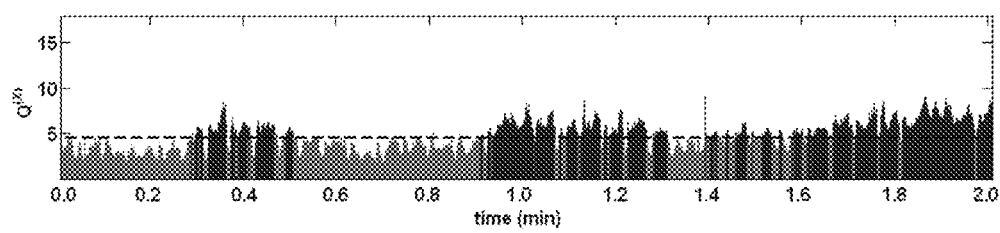
Figure 4:
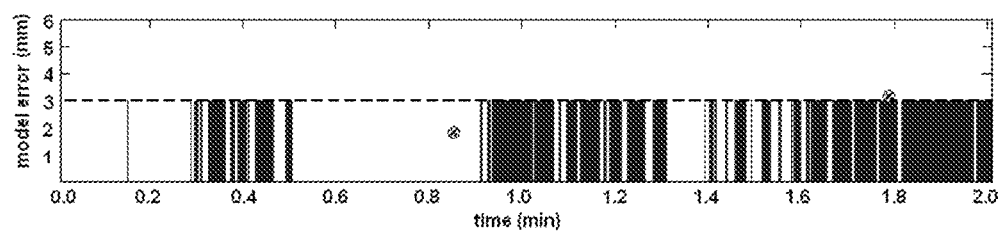

Applying a confidence limit-based threshold made it possible to detect errors >3 mm with a high degree of sensitivity (>90%). As shown in the ROC curves of FIG. 4, varying α led to a tradeoff between sensitivity and specificity. In the context of this application, sensitivity refers to the probability that a large error will be detected by the SPC method. Thus, as described above, this study focused on parameters leading to high (90-95%) sensitivity and decreased (13-24%) specificity. Low specificity indicates an increased rate of false positives. In this application, false positives correspond to unnecessary image acquisitions. To investigate the impact of this relatively low specificity on clinical workflow, this study described the time to alarm for 90-95% sensitivity.

The mean time to alarm for 90-95% sensitivity was 4-8 min, representing a four- to eight-fold decrease in radiographic image acquisition frequency over the Cyberknife Synchrony™ method. Because there was considerable variability in the time to errors >3 mm, acquiring radiographic images at a preselected regular interval often would result in missing large errors. For this dataset, the Cyberknife Synchrony™ system localized the tumor via radiographs every third beam delivered, with a mean interval of 63 sec between image acquisitions. The current version of the Cyberknife Synchrony™ allows the operator to select a constant time interval of up to 2.5 min between radiographic image acquisitions. This maximum time interval for the Cyberknife Synchrony™ system is more than double the average frequency of the proposed $T^2 \cup Q^{(X)}$ method as described above.

This study determined the performance of SPC monitoring for predicting PLS-based tumor localization errors. Malinowski K, McAvoy T J, George R, et al. Mitigating errors in external respiratory surrogate-based models of tumor position. [In press]. The described method can be implemented in any other tumor displacement inferential approaches to minimize the imaging frequency of existing systems, thereby decreasing treatment interruptions and overall patient treatment time. Through monitoring of surrogate measurement data, the examples described above may have increase the targeting accuracy of any real-time motion compensation device, including radiation gating systems. Generally, gating margins based on a single simulation session at the beginning of the treatment may not be enough to evaluate residual motion of a gated treatment.

However, respiratory surrogate monitoring through $T^2$ and $Q^{(X)}$ can detect increases in residual motion during the treatment, allowing the clinicians to pause treatment to collect radiograph images when necessary to ensure that tumor motion is in accordance with the internal margin for the plan.

In many cases, the Hotelling statistic ($T^2$) and the input variable squared prediction error ($Q^{(X)}$) both exceeded confidence limit thresholds together. Ergon R. Informative PLS score-loading plots for process understanding and monitoring. Journal of Process Control. 14, 889-897 (2004). In some cases $T^2$ indicated large error first, but in other cases $Q^{(X)}$ indicated large error first. As a result, combining the metrics resulted in a slight increase in performance of the method. Mathematically, $T^2$ and $Q^{(X)}$ are independent and concurrent increase is indicative of a change in the tumor-surrogate relationship. Transient and long-term changes in the tumor-surrogate relationship have been described as shifts in the phase offset between tumor and surrogate motion, baseline drifts in tumor position or surrogate signal, or other complex behavior leading to lapses in correlation. See Ozhasoglu C, Murphy M. Issues in respiratory motion compensation during external-beam radiotherapy. Int. J. Radiat. Oncol. Biol. Phys. 52, 1389-99 (2002); Hoisak J D P, Sixel K E, Tirona R, et al. Correlation of lung tumor motion with external surrogate indicators of respiration. Int. J. Radiat. Oncol. Biol. Phys. 60, 1298-1306 (2004); Seppenwoolde Y, Shirato H, Kitamura K, Shimizu S, van Herk M, Lebesque J V, Miyasaka K. Precise and real-time measurement of 3D tumor motion in lung due to breathing and heartbeat, measured during radiotherapy. Int. J. Radiat. Oncol. Biol. Phys. 53, 822-834 (2002); andIonascu D, Jiang S B, Nishioka S, et al. Internal-external correlation investigations of respiratory induced motion of lung tumors. Med. Phys. 34, 3893-3903 (2007).

The example methods described above resembles statistical process control (SPC) monitoring utilized in chemical process control applications. See Ergon R. Informative PLS score-loading plots for process understanding and monitoring. Journal of Process Control. 14, 889-897 (2004); Jackson J E and Mudholkar G S. Control procedures for residuals associated with principal components analysis. Technometrics. 21, 341-349 (1979); and Lee J, Yoo C, Lee I. Statistical monitoring of dynamic processes based on dynamic independent component analysis. Chem Eng Sci. 59, 2995-3006 (2004). However, in classical SPC, metrics are derived directly from the model that is being monitored. By contrast, in this example method creates a target position model and models to monitor the treatment. For optimal tumor localization accuracy, surrogate marker data was projected from 3D to 1D. This reduction in input dimensionality of the measurement data from m=9 to m=3 reduced the number of scores available for calculating $T^2$, which uses scores 1 to A, and $Q^{(X)}$, which uses scores A+1 to m. As a result, reducing input dimensionality from 9 to 3 decreased the specificity, and consequently the time to alarm, for a given sensitivity. For instance, by utilizing the 3D (9 input) marker data for monitoring 3 surrogate markers, at 95% sensitivity the mean time to alarm increased from 2-4 min to 4-8 min.

Neither $T^2$ nor $Q^{(X)}$ increased monotonically over time. The $T^2$ statistic was cyclic in nature, increasing during certain phases of respiration, and both $T^2$ and $Q^{(X)}$ were associated with some degree of noise. In another example, it may be possible to reduce this periodicity by selecting training data encompassing a wide range of respiratory phases. It was possible to improve specificity for $Q^{(X)}$ and $T^2 \cup Q^{(X)}$ by considering time trends in $T^2$ and $Q^{(X)}$ values. Utilizing multiple surrogate marker data samples (1-3 sec of data from 26 Hz measurements) may have helped overcome the effects of both noise and training data selection. However, averaging the $T^2$ and $Q^{(X)}$ signals using an exponentially-weighted moving average did not improve the instantaneous large error detection.

A second study below is related to a comparison of the example processes described above in comparison to conventional techniques to update the system to determine when to perform a localization and update the target position model.

Methods and Materials

Data

A database of Cyberknife Synchrony™ system log files was analyzed. 121 treatment fractions of lung tumor motion data from 61 patients and 45 treatment fractions of pancreas tumor motion data from 23 patients were considered. Each log file consisted of two sets of recordings that were aligned using system-recorded timestamps: (1) intermittent measurements of tumor position, as localized through identification of the centroid of 2-3 implanted fiducial markers in stereoscopic radiographs; and (2) frequent (26 Hz) measurements of the positions of a set of three LED markers affixed to a form-fitting vest. Stereoscopic radiographs were captured once every three beams for a mean frequency of about once per minute. From these datasets the inventors extracted concurrent internal (tumor) and external (marker) localizations at each radiographic measurement.

Target Motion Prediction

For each treatment fraction, a regression model was created to predict target positions, Y, from the external surrogate marker data, R. The initial model was created from the first 6 radiographic tumor localizations in each treatment fraction.

Three one-dimensional PLS inputs were derived from the external surrogate measurement data (i.e., one for each of the three external surrogate markers). Raw input data, X, was a matrix combining three clusters of inputs such that $X=[X_1, X_2, X_3]$, where $X_m$ was an n×3 matrix of 3D marker positions at n times. Each matrix of marker motion, $X_m$, was projected onto a single dimension, $R_m$, according to the first principal component vector, $P_m$, of $X_m$. Each row of $R_m$, $R_{mi}$, was projected according to $R_{mi}=(X_{mi}-\overline{X}_m) \cdot P_m$, where $\overline{X}_m$ is the 1×3 mean of $X_m$ along its columns. The projected inputs, $R_m$, were recombined into an n×3 processed-input matrix, R, as $R=[R_1, R_2, R_3]$.

The SIMPLS PLS regression algorithm was used to develop the target position model. Stated briefly, the SIMPLS algorithm decomposes inputs, R, and outputs, Y, into $R=T \cdot W^T$ and $Y=U \cdot Q^T$. The latent variables T and U are compressed into $\hat{T}$ and $\hat{U}$, which are composed of the columns 1 to A of matrices T and U, respectively. The weight variables are compressed into $\hat{W}$ and $\hat{Q}$, comprising rows 1 to A of W and Q, respectively. Cross-validation was used to select the appropriate number of PLS factors, A, for each training dataset. The regression process minimizes the expression $$\frac{1}{2} B^T \cdot R^T R \cdot B - (R^T Y)^T \cdot B$$

to yield a target position model of the form $\hat{Y}=R \cdot B$ for surrogate inputs, R, estimated target position, $\hat{Y}$, and PLS-derived regression coefficient matrix, B. The radial inferential model error, e, at each sample, i, was calculated as $e_i=$ $\sqrt{\Sigma(\hat{y}_i - y_i)^2}$ for tumor positions predicted by the model ($\hat{y}_i$) and measured using radiographs ($y_i$).

Model Monitoring and Updates
Respiratory Surrogate Analysis

The behavior of the external surrogate markers was characterized during the model training period and re-evaluated over the course of the treatment fraction.

For each set of 6 training data samples, a second PLS model based on target position outputs, Y, and raw (unprojected) surrogate marker positions, X, was created. This process yielded a new set of regression coefficients and target position estimates such that $\tilde{Y} = \tilde{B} \cdot X$.

The input matrix X was comprised of n rows, $z_i$ for i=1 to n, such that $X = [z_1, z_2, \ldots, z_n]^T$, and each row represented the surrogate markers' positions at a single point in time. For each set of surrogate marker displacements, $z_i$, an associated score vector, $\hat{t}_i$, was calculated as $\hat{t}_i^T = z_i \cdot \hat{W}$. The scores were then used to calculate the Hotelling statistic, $T^2$, and the input variable squared prediction error, $Q^{(X)}$, for sample i. $T^2$ and $Q^{(X)}$ are complementary, independent statistical metrics. Once the PLS measurement monitoring model is created from a training dataset of 6 samples, the surrogate-based metrics are calculated from measurements of the surrogate markers and do not utilize radiographic measurements of target position.

Hotelling's $T^2$ statistic[16] measures the variation in the measurement data scores. Aberrant $T^2$ values indicate that the relationship between latent variables has changed and that the model must be extrapolated to fit new measurement data. $T^2$ was calculated as $T_i^2 = t_i^T \cdot S^{-1} \cdot t_i$ from the estimated training data score covariance matrix, $S_i = \hat{T}_i^T \cdot \hat{T}_i / (n-1)$. The $(1-\alpha)$ percentile confidence limit on $T^2$ was calculated as $$T_\alpha^2 = \frac{(n^2-1)A}{n(n-A)} F_\alpha(A, n-A),$$

n=6 was the number of training samples used to generate the measurement monitoring model, A=1 was the number of scores in the PLS model, and $F_\alpha(A, n-A)$ was the upper (100%) ($\alpha$) critical point of the F distribution with (A, n-A) degrees of freedom.

The input variable squared-prediction-error, $Q^{(X)}$, measures the amount of data in the input residuals after the compression of raw inputs into scores. See Hoisak J D P, Sixel K E, Tirona R, et al. Correlation of lung tumor motion with external surrogate indicators of respiration. Int. J. Radiat. Oncol. Biol. Phys. 60, 1298-1306 (2004). $Q^{(X)}$ was given by $$Q_i^{(X)} = \sum_{j=A+1}^{n} (\hat{z}_{ij} - z_{ij})^2,$$

where $\hat{z}_i = t_i \cdot \hat{W}$ represents the surrogate marker measurement vector, $z_i$, compressed to A latent variables. Confidence limits on $Q^{(X)}$ were calculated through the Jackson-Mudholkar[11] formula, $$Q_\alpha = \theta_1 \left[ 1 - \frac{\theta_2 h_0 (1-h_0)}{\theta_1^2} + \frac{z_\alpha \sqrt{2\theta_2 h_0^2}}{\theta_1} \right]^{1/h_0},$$

in which $z_\alpha$ is the upper (100%) ($\alpha$) critical point of the normal distribution, $$\theta_j = \sum_{k=A+1}^{N} \lambda_k^j, \; h_0 = 1 - \frac{2\theta_1 \theta_3}{3\theta_2^2},$$

and $\lambda_k$ is the kth eigenvalue of $(\hat{z}_{new,i})^T (\hat{z}_{new,i} - z_{new,i})$.

Model Update Schema

The target localization accuracy of the respiratory surrogate models was evaluated for four possible update methods described below. Each method was tested against 20 min of data following the initial 6-sample training dataset.

Never Update: Currently, despite possible tumor-surrogate relationship changes during treatment, most clinics do not update the surrogate models. To simulate this case, the initial model is based on the first 6 measurements in the treatment fraction for the entire 20 min testing dataset.

Always Update: To evaluate the opposite extreme, the inventors updated the model at each target localization (separated by an average of 63 sec) in the log files. Specifically, 1 sec after a radiographic tumor localization, the 6 most recent radiographic measurements were used to train a new target position model from the surrogate marker positions. This target position model was then applied to predict tumor position up to the next update, 1 sec after the next radiographic target localization.

Error-Based Update: The Cyberknife Synchrony™ system periodically captures radiographs to validate its respiratory-surrogate model. The radiographically measured target position is compared to the position determined by the target position model. If the difference between the measured position and the determined target position (i.e., the localization error) exceeds a user-set threshold such as 3 mm, the target position model is updated. See Seppenwoolde Y, Berbeco R I, Nishioka S, Shirato H, Heijmen B. Accuracy of tumor motion compensation algorithm from a robotic respiratory tracking system: a simulation study. Med. Phys. 34, 2774-2784 (2007). To simulate this process, a new target position model was created each time the localization error exceeded 3 mm. An updated target position model was applied to data acquired 1 second after the each tumor localization error was greater than 3 mm.

Respiratory Surrogate-Based Update: Rather than base the decision of whether to update a model on target localizations using radiographic images, the respiratory surrogate method is based on external measurements from the surrogate markers. The $T^2$ and $Q^{(X)}$ values were evaluated for each set of surrogate marker measurements. If either $T^2$ or $Q^{(X)}$ of a sample exceeded the $70^{th}$ percentile $T^2$ or $Q^{(X)}$ confidence limit, then a new target position model was created from the previous 6 radiographic localizations. This target position model was applied to data in the fraction following 1 sec after either $T^2$ or $Q^{(X)}$ exceeded its confidence limit threshold.

Results

Figure 6:
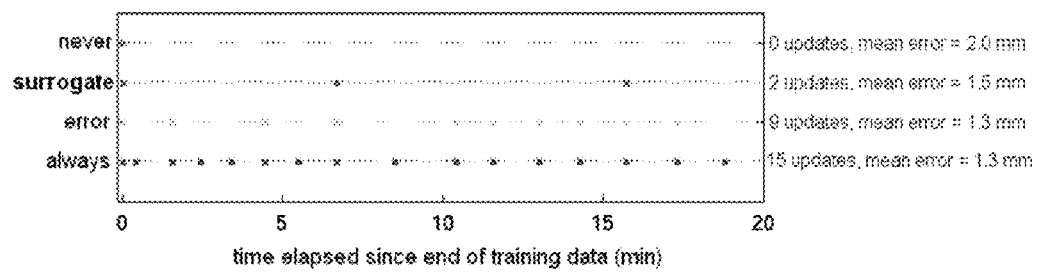
FIG. 6 depicts timing model updates for four update methods in a representative treatment fraction.

While updates for this dataset were limited to the times at which radiographs were acquired, the update timings differed based on the four methods. FIG. 6 shows the mean error for the never update method was 2.0 mm. The mean error for the error-based method and the always update method were 1.3 mm. The mean error for the surrogate-based method was 1.5 mm. This demonstrates that frequent updates do not always correspond to more accurate tumor motion prediction.

Figure 7:
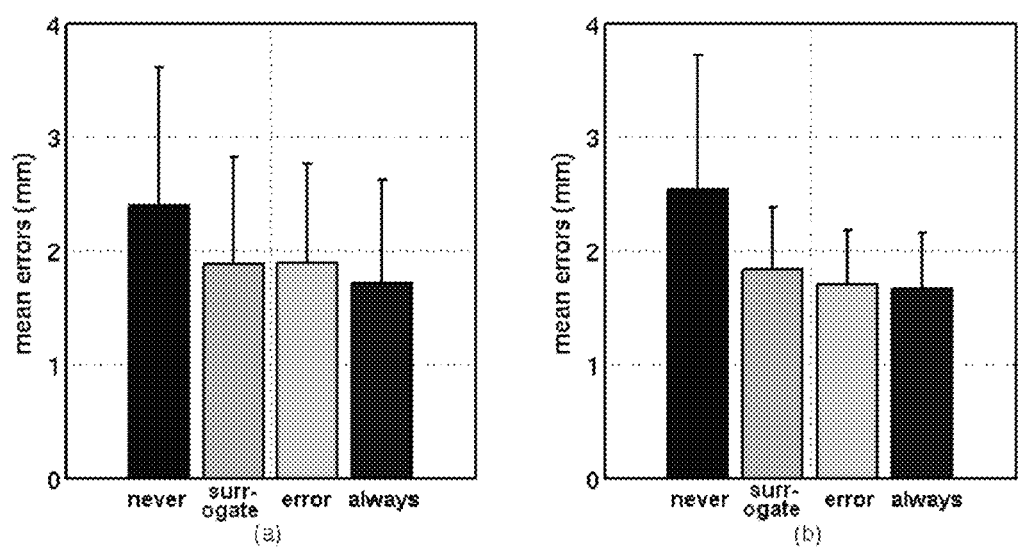
FIG. 7 depicts mean and standard deviation tumor position prediction errors over 20 minutes for the update methods.

Model Errors: Radial target localization errors (mean±standard deviation) illustrated in FIG. 7 for the never update, the surrogate-based update, the error-based update, and the always update schema were 2.4±1.2 mm, 1.9±0.9 mm, 1.9±0.8 mm, and 1.7±0.8 mm, respectively. For never, surrogate-based, error-based, and always update methods, respectively, 7%, 3%, 3%, and 3% of tumor position prediction errors exceeded 5 mm, and 26%, 14%, 11%, and 13% exceeded 3 mm. Error distributions for update schema other than never-update did not differ significantly from one another (t-test, p>0.05). However, the never update tumor localization errors were significantly larger (t-test, p<0.05) than those of the other update methods.

Figure 8:
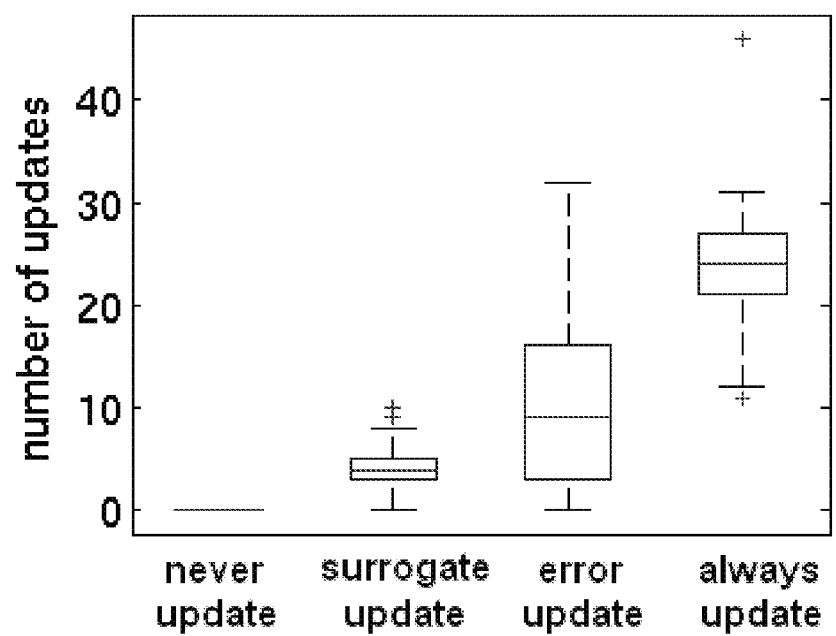
FIG. 8 depicts the number of model updates for a sample 20 minute dataset for the update methods.
Figure 9:
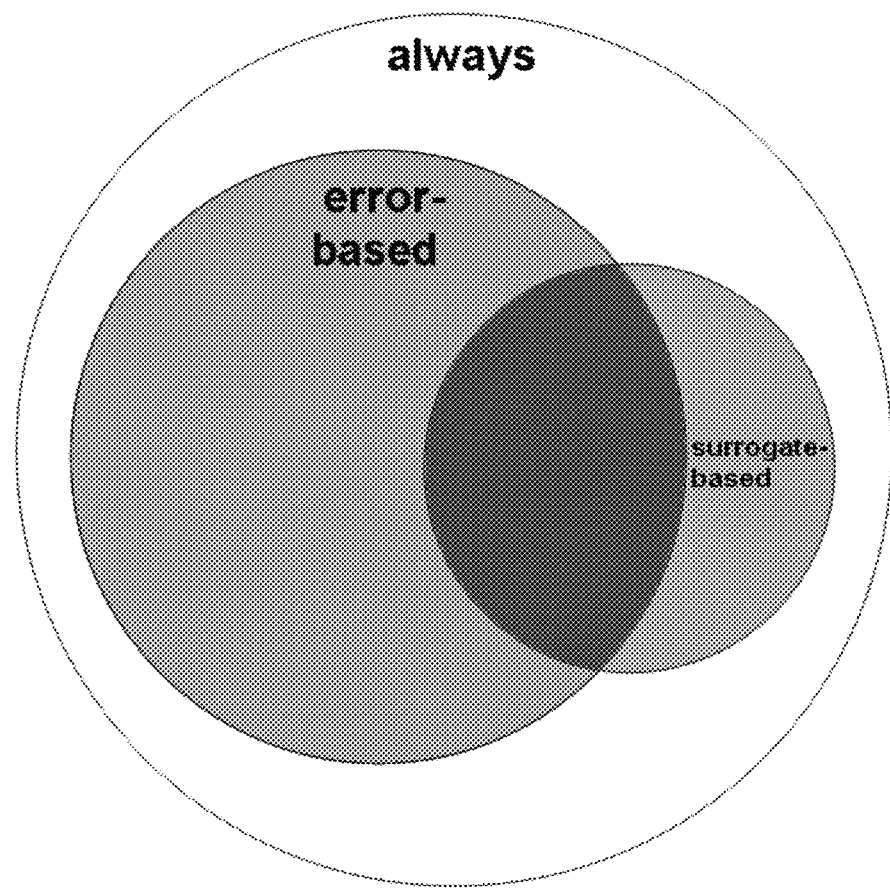
FIG. 9 is a Venn diagram depicting the relative number of updates over an entire sample dataset and the proportions of samples for which updates under the always, error-based, and/or surrogate-based update methods were concurrent.

Update Timing: FIG. 8 illustrates that the median numbers of updates over the course of 20 min were 0, 4, 9, and 24 for never, surrogate-based, error-based, and always update schema, respectively. There were significant (t-test, p<0.05) differences in quantities of updates between each of the four methods. 24% of the target localizations associated with an error-based update were also associated with a surrogate-based update (FIGS. 9), and 55% of tumor localizations that were associated with surrogate-based updates corresponded to simultaneous error-based updates.

Site-Specific Results: Neither mean error nor number of updates were significantly associated with the targets in either the lungs on pancreas (two-way ANOVA, p>0.05).

Discussion

As disclosed herein, an intelligent target position model update timing results in an accurate target position model while limiting its update frequency. The results of this example illustrate that more frequent updates to the target position model do not guarantee more accuracy. While any method of updating resulted in smaller target localization errors than no model updates at all, the localization errors were not significantly different across the three update methods (surrogate-based, error-based, or always update). However, the mean number of updates of the model updates in 20 minutes was 4 for the surrogate based, 9 for the error-based update, and 24 for the always update schemas.

The prediction accuracy of respiratory surrogate-based tumor localization models degrades over the course of a treatment fraction. As described above, the $T^2$ and $Q^{(X)}$ statistics predict large respiratory target position model errors with high sensitivity (95%) but limited specificity (15%). This example shows that instantaneous error may not be the best method to determine to update a model. By updating the target position model each time a localization error exceeded the threshold of 3 mm, many updates to the target position model were carried out without significant improvement to mean accuracy. Over the course of a fraction, the surrogate method was associated with more localization errors >3 mm than the error-based method (14% vs. 11% of localizations), but for both methods only 3% of errors were >5 mm. However, the error-based method required more than twice as many updates as the surrogate-based method. Thus, frequent updates to the target position model do not necessarily lead to a more accurate model. See Seppenwoolde et al. Med. Phys. 34, 2774-2784.

In both the error-based and the surrogate-based update methods, parameters can be selected to tradeoff between tumor localization error and number of updates. For error-based updates, 3 mm was used as the threshold because it has been cited as a clinically utilized error threshold for the Cyberknife Synchrony™ system. See Seppenwoolde et al. Med. Phys. 34, 2774-2784. The surrogate metrics' confidence limits were set to the $70^{th}$ percentile expected value, such that the accuracy was not significantly different than the error-based method. This allowed a direct comparison of the number of updates for the two methods when target localization errors were equal. For either technique, a larger localization error tolerance would necessitate fewer updates.

As noted above, the number of updates was evaluated for 20 min of data. For many modern treatments, actual exposure to the radiotherapy treatment is less than 20 min, but in-room time can be longer. In one example, the patient is usually on the couch for about 20 min for conventionally fractionated treatments and for about 30 min for stereotactic body radiotherapy treatments. In practice, model update implementation would be implemented differently on each system, but it is likely that the process of capturing images for new model-building data during an update would take some time, potentially extending the duration of the treatment fraction. A shorter treatment would require fewer updates. Thus, even with respiration monitoring, it is important to complete a treatment fraction, including the setup process, as quickly as possible.

The surrogate-based monitoring method explored described above was applied to PLS respiratory surrogate models. The $T^2$ and $Q^{(X)}$ metrics are based on the scores developed as part of the PLS regression process. However, it would be possible to monitor any multiple-input surrogate model using the described examples. In particular, because the PLS output is very similar to that of the Cyberknife Synchrony™ system, it is likely that the surrogate-based monitoring method evaluated in this study could be implemented in the Cyberknife Synchrony™ tumor localization algorithm. Accurate tumor localization is essential and a knowledge-based method for model update timing could improve system performance. This type of monitoring would also benefit gating technologies. Berbeco et al. and Cai et al. have shown that breath-to-breath variations even in the relatively stable end-exhale position necessitate use of an internal margin for gated treatments.

The surrogate-based update uses respiratory surrogate measurements alone. By contrast, the error-based method requires concurrent respiratory surrogate measurements and radiographic images to validate the model directly. For this work, to allow validation of the method, updates were limited to the moments at which radiographic target localizations were available (about once per minute). However, because the surrogate-based update method does not require internal localization, it has the potential to give early warnings of large errors by checking for updates at the surrogate measurement rate (26 Hz in this dataset).

With no model updates, mean tumor localization errors were 2.4 mm, and 26% of errors exceeded 3 mm. With the update methods, mean errors were reduced to 1.7-1.9 mm, and 11-14% of errors exceeded 3 mm. Differences in errors between surrogate-based, error-based, and always update methods were not significant, but the number of updates in a fraction varied considerably with update method. On average, the surrogate method required 44% as many updates as the error method and 17% as many updates as the always-update method.

All documents, books, manuals, papers, patents, published patent applications, guides, abstracts and other reference materials cited herein are incorporated by reference in their entirety. While the foregoing specification teaches the principles of the present invention, with examples provided for the purpose of illustration, it will be appreciated by one skilled in the art from reading this disclosure that various changes in form and detail can be made without departing from the true scope of the invention.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of this invention.

What is claimed is:

1. A method for indirectly monitoring the position of a target inside a body, the method comprising:
    generating position data associated with one or more surrogate devices;
    predicting a location of the target from the position data based on a target position model that establishes a relationship between an actual location of the target and the position data;
    determining, using an analysis of an error prediction model, accuracy of the relationship between an actual location of the target and the position data; and
    determining that the predicted location of the target deviates from the actual location of the target when the analysis of the error prediction model results in a confidence threshold being exceeded.

2. The method recited in claim 1, further comprising delivering a medical treatment to the predicted location of the target.

3. The method recited in claim 2, wherein said generating position data comprises receiving a signal from the one or more surrogate devices attached to the body and generating the position data from the received signal.

4. The method recited in claim 2, further comprising
    receiving calibration position data and images of the target, wherein the calibration position data and the images are synchronized over a period of time,
    determining target site positions of the target from the received images, and
    generating the target position model by determining a correlation between the calibration position data and the determined target site positions.

5. The method recited in claim 2, further comprising, if the predicted location of the target deviates from the actual location of the target, pausing the delivering of the medical treatment, updating the target position model, and further delivering the medical treatment.

6. The method recited in claim 2, wherein the analysis of the error prediction model includes a statistical analysis that determines whether the relationship between the actual location of the target and the position data has changed.

7. The method recited in claim 6, wherein the statistical analysis includes a Hotelling and Q-statistic.

8. The method recited in claim 2, wherein the analysis of the error prediction model includes a statistical analysis that determines an amount of variance in the position data not captured by the target position model.

9. The method recited in claim 8, wherein the statistical analysis includes an input variable squared prediction error.

10. The method recited in claim 2, wherein the error prediction model determines whether the predicted location of the target deviates occurs during a treatment period using only the position data.

11. A system for indirectly monitoring the position of a target inside a body, the system comprising:
    a sensor device configured to provide position data; and
    a processor for (i) predicting a location of the target from the position data using a target position model that establishes a relationship between the target and the position data, (ii) determining, using an analysis of an error prediction model, accuracy of the relationship between an actual location of the target and the position data, and (iii) determining that the predicted location of the target has deviated from the actual location of the target when the analysis of the error prediction model results in a confidence threshold being exceeded.

12. The system recited in claim 11, further comprising a treatment device configured to deliver a medical treatment to the predicted location of the target of the body for a treatment period.

13. The system recited in claim 12, wherein the sensor device receives a signal from the one or more surrogate devices attached to the patient and generates the position data based on the received signal.

14. The system as recited in claim 12, wherein, if the predicted location of the target has deviated from the actual location of the target, the processor controls the treatment device to stop delivering the medical treatment, updates the target position model, and controls the treatment device to start delivering the medical treatment again.

15. The system recited in claim 12, wherein the analysis includes a statistical analysis that determines if the relationship between the actual location of the target and the position data has changed.

16. The system recited in claim 15, wherein the statistical analysis includes a Hotelling and Q-statistic.

17. The system recited in claim 12, wherein the analysis includes a statistical analysis that determines an amount of variance in the position data not captured by the target position model.

18. The system recited in claim 17, wherein the statistical analysis includes an input variable squared prediction error.

19. The system recited in claim 12, wherein the processor uses the error prediction model to determine whether the predicted location of the target has deviated during the treatment period using only the position data.

20. A method of indirectly monitoring the position of a target inside a body, the method comprising:
    generating a target position model that predicts a location of a target of a patient and generating an error prediction model used to determine accuracy of the predicted location of the target;
    generating position data based on the respective positions of one or more surrogate devices coupled to the patient;
    predicting a location of the target using the target position model and the position data;
    delivering a medical treatment to the patient based on the target position model during a treatment period;
    determining whether the predicted location of the target has deviated from the actual location of the target using only the position data and the error prediction model during the treatment period; and
    when the predicted location of the target has deviated from the actual location of the target, pausing delivering of the medical treatment, updating the target prediction model, and resuming the delivering of the medical treatment.

* * * * *